United States Patent
Mendiretta et al.

(10) Patent No.: US 8,507,221 B2
(45) Date of Patent: Aug. 13, 2013

(54) PROCESS FOR THE EXPRESSION OF PEPTIDES OF INTEREST USING GCSF AS A FUSION PARTNER

(75) Inventors: Sanjeev Kumar Mendiretta, Gujarat (IN); Pankaj R. Patel, Gujarat (IN); Sanjay Bandyopadhyay, Gujarat (IN); Vibhor Saraswat, Gujarat (IN); Arun Kumar Singh, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 309 days.

(21) Appl. No.: 12/679,346

(22) PCT Filed: Sep. 22, 2008

(86) PCT No.: PCT/IN2008/000599
§ 371 (c)(1),
(2), (4) Date: Jun. 21, 2010

(87) PCT Pub. No.: WO2009/066320
PCT Pub. Date: May 28, 2009

(65) Prior Publication Data
US 2012/0142891 A1      Jun. 7, 2012

(30) Foreign Application Priority Data
Sep. 21, 2007   (IN) .......................... 1848/MUM/2007

(51) Int. Cl.
*C07K 14/535* (2006.01)
*C07K 14/62* (2006.01)
*C07K 14/635* (2006.01)
*C12P 21/02* (2006.01)

(52) U.S. Cl.
USPC ..... 435/69.1; 435/69.4; 435/69.51; 435/69.6; 435/68.1; 435/320.1; 435/226; 530/300; 530/395

(58) Field of Classification Search
None
See application file for complete search history.

(56) References Cited

FOREIGN PATENT DOCUMENTS
WO      2007/091250 A      8/2007
WO      2007/102174 A      9/2007

OTHER PUBLICATIONS

Lee et al. Biotechnology Letters, 2003, vol. 25, pp. 205-211.*
Cox et al Experimental Hematology, 2004, vol. 32, pp. 441-449.*
Cheon Soon Bae, et al.; Enhanced Secretion of Human Granulocyte Colony-Stimulating Factor Directed by a Novel Hybrid Fusion Peptide From Recombinant *Saccharomyces cerevisiae* at High Cell Cencentration; Biotechnology and Bioengineering Mar. 5, 1998; vol. 5; No. 5; Mar. 5, 1998; pp. 600-609; XP002536134; ISSN: 0006-3592; p. 601, right-hand column—p. 602; left-hand column; figure 1.

* cited by examiner

*Primary Examiner* — Bridget E Bunner
*Assistant Examiner* — Fozia Hamud
(74) *Attorney, Agent, or Firm* — Ladas & Parry LLP

(57) ABSTRACT

The present invention discloses an improved process for the production of desired recombinant peptides from bacterial cells by using G-CSF as a novel fusion partner for their high level expression in these cells. The invention further provides an expression system comprising the fusion protein wherein the G-CSF is operatively linked to the peptide of interest via an enzymatic or chemical cleavage site which can be used to separate the fusion partner from the said peptide.

27 Claims, 1 Drawing Sheet

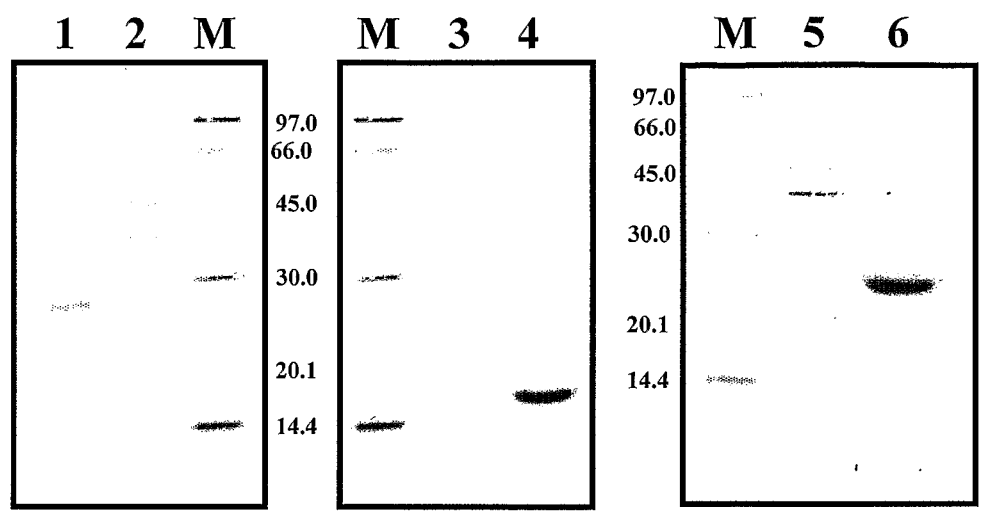
| Lane | Sample |
|---|---|
| M | LMW marker |
| 1 | Proinsulin Induced |
| 2 | Proinsulin Uninduced |
| 3 | Angiotensin uninduced |
| 4 | Angiotensin induced |
| 5 | PTH proinduced |
| 6 | PTH induced |

PROCESS FOR THE EXPRESSION OF PEPTIDES OF INTEREST USING GCSF AS A FUSION PARTNER

FIELD OF THE INVENTION

The present invention relates to the field of production of recombinant peptides. More specifically the present invention discloses an improved method for the production of desired recombinant peptides from bacterial cells by using G-CSF as a novel fusion partner for their high level expression in these cells. The invention further provides an expression system comprising the fusion protein wherein the G-CSF is operatively linked to the peptide of interest via an enzymatic or chemical cleavage site which can be used to separate the fusion partner from the said peptide.

BACKGROUND OF THE INVENTION

Peptides are heteropolymers of amino acids that are linked via their carboxyl and amino groups by amide bonds. Since the above definition holds true for proteins as well, they are often differentiated from proteins based upon their chain length, being usually described as those heteropolymers that are ranging in chain length from two to a few to several dozen amino acid residues.

Some examples of these peptides that vary vastly in their molecular weight and their functions are described here [Geysen, H. M. et al, *J. Immunol. Methods*, 102:259-274. (1987); Milich, D. R. *Semin. Immunol.*, 2(5):307-315 (1990); Cochran, A. G. *Chemistry & Biology*, 7:R85-R94 (2000)]. The active peptide, insulin (51 residues, 5773 Da), formed after processing of the larger but inactive peptide, pro-insulin (86 residues), plays a critical role in glucose metabolism in the body and lack of it leads to type I diabetes. Parathyroid hormone (84 residues) is the most important endocrine regulator of the levels of calcium and phosphorus in the blood. A much smaller version of the parathyroid hormone, teriparatide (34 residues), is sold by Eli Lilly for the treatment of osteoporosis. Calcitonin (32 residues) also plays a critical role in calcium metabolism and has opposite effects with respect to the parathyroid hormone. It is also used in the treatment for osteoporosis. Angiotensin I, II, III and IV having 10, 8, 7 and 6 residues respectively, have diverse roles as endocrine, paracrine, and intracrine hormones, causing vasoconstriction, increasing blood pressure and causing release of aldosterone from the adrenal cortex. The non-caloric sweetener, aspartame (a dipeptide of aspartic acid and esterified phenylalanine) is used as a sugar substitute. These examples illustrate the vast diversity of functions, chain length and utility amongst peptides. Their role as mediators of key biological functions e.g., as hormones, enzyme substrates or inhibitors, neurotransmitters, immunomodulators and, antiviral agents make them particularly attractive as therapeutic agents. More than 40 therapeutic peptides are available in the world market today and more than 400 peptides are in advanced pre-clinical phases of drug development worldwide [Parmar, H. Therapeutic Peptides in Europe: Finding the Opportunities, *Frost and Sullivan Market Insight*, Nov. 26, 2004]. Therefore the therapeutic application of peptides has an enormous potential.

Originally peptides of therapeutic significance used to be isolated from biological tissues. For example, insulin was produced from the ox pancreas [Collip, J. *J. Physiol.*, 66:416-430 (1928)], and Calcitonin from the ultimobronchial glands of fish [(Parkes, Colo. et al., *Fed. Proc.*, 28:413 (1969)]. The tissue origin of these peptides made the isolation methods difficult and cumbersome, yielded non-ideal product purity, carried the risk of transmitting infections and generally affected the commercial scalability, ultimately limiting the commercialization of peptides as therapeutics.

Chemical method is one of the solutions to the above problem of commercial production—at least for the production of small and medium sized peptides ranging from about 5 to 80 residues [Kimmerlin, T. and Seebach, D. *J. Pept. Res.*, 65(2):229-260 (2005)]. But this method also has many disadvantages that make it inefficient in cost, such as, the possibility of racemization, poor solubility of protected peptide fragments, limitation on the length of peptide and serial side reactions. The undesirable side reactions associated with this method decrease the yield and render necessary, difficult and lengthy purification procedures. Therefore, even though chemical synthesis is the most mature technology for peptide synthesis today, it is fraught with problems that add to the overall cost of their production signifying the need for developing other distinctly different methods of their production.

In principle a large number of the above problems can be solved by employing the recombinant DNA technology that allows the selection, amplification and manipulation of expression of endogenous and foreign genes in microbial cells. This technology is better than the chemical technology in that it naturally produces non-racemic and fully correct a.a. sequences, as nature has evolved living organisms to do so. Further this technology also allows more environmentally friendly processes of production and purification. However, this technology is limited by the fact that in general, it is not possible to get high levels of expression of peptides in a microbial host. Because of their short length, peptides get easily degraded by the *E. coli* proteolytic machinery [Marston, F. A. *Biochem. J.*, 240:1-12 (1986); Makrides, S. C. *Microbiol. Rev.*, 60:512-538 (1996)]. Many eukaryotic foreign peptides are recognized as abnormal in *Escherichia coli* and get rapidly degraded in the expression host [Goldschmidt, R. *Nature*, 228:1151-1154 (1970); Lin, S. & Zabin, I. *J. Biol. Chem.*, 247:2205-2211 (1972)]. The half-life of human proinsulin in *E. coli* has been reported to be only 2 minutes [Talmadge, K. & Gilbert, W. *Proc. Natl. Acad. Sci. USA*, 79:1830-1833 (1982)].

A common strategy to overcome the problem of degradation of peptides in the expression host is to express them as fusion proteins in conjunction with another larger peptide or protein, which acts as a fusion partner. After expression, the peptide and the fusion partner are separated from each other by chemical or proteolytic cleavage at a site which was pre-designed into the fusion product. In this regard many proteins have been used as fusion partners that produce the fusion product in both soluble and insoluble form inside the cell. Ray et al., [Ray, M. V. L., et al., *Bio/Technology*, 11:64-70 (1993)] describe the use of glutathione-S-transferase (GST) as a fusion partner to get soluble intracellular expression in *E. coli* of salmon calcitonin which was cleaved away from the fusion protein with cyanogen bromide. Dykes et al., [Dykes, C. W. et al., *Eur. J. Biochem.*, 174:411-416 (1988)] describes the soluble intracellular expression in *E. coli* of a fusion protein consisting of a human atrial natriuretic peptide and chloramphenicol acetyltransferase, where the fusion protein was either proteolytically cleaved by thrombin or enterokinase or chemically cleaved with 2-(2-nitrophenylsulphenyl)-methyl-3'-bromoindolenine to release the peptide of interest. Maltose-binding protein and thioredoxin have also been used as solubilizing fusion partners [Baneyx, F. *Curr. Opin. Biotechnol.*, 10:411-421 (1999)]. Another example is that of U.S. Pat. No. 5,223,404 which describes the use of ompA as a fusion partner with PTH (1-34) in order to get the expression of soluble protein in periplasmic space.

While in many cases the soluble fusion product yields good expression [Cipakova, I. et al., *Protein Expr. Purif,* 37:207-212 (2004); Forrer, P. & Jaussi, R. *Gene,* 224:45-52 (1998); Hoffman, F. et al., *Enz. and Microb. Technol.,* 34:235-241 (2004); Baneyx, F. *Curr. Opin. Biotechnol.,* 10:411-421 (1999)] and also keeps the fused protein in its correct folding conformation [Marco, V. D. et al., *Biochem. Biophys. Res. Commun.* 322:766-771 (2004); Zou, Z. et al., *Journal of Biotechnology,* 135:333-339, (2008)] this technology has remained commercially unattractive. This is because in the cytoplasm the product is present along with hundreds or thousands of other host proteins making the process of purification extremely expensive and inefficient. On the other hand soluble expression in the periplasm is limited by the small size of this space. Therefore, it is not surprising to note that commercial examples of soluble expression of peptides are rare, if not entirely non-existent. To circumvent these problems peptides are often produced as insoluble fusion products that form inclusion bodies due to the precipitation and aggregation of the proteins with in the cell [Williams, D. C. et al., *Science* 215:687-688 (1982)]. The formation of inclusion bodies provides several advantages for commercial production of proteins. The inclusion bodies not only prevent the degradation of the expressed protein by protecting the product of interest from the action of cellular proteases (Singh, S. M. and Panda, A. K., *J. Biosci. Bioengg.* 99(4):303-310 (2005)], but also ensure that the product is produced in relatively very high level of purity [Panda, A. K. *Adv. Biochem. Engg./Biotechnol.* 85:43-93 (2003)]. The difference in size and density of inclusion bodies as compared to cells results in easy isolation of these inclusion bodies from the cells [Bowden, G. A. et al., *Bio/Technol.* 9:725-730 (1991)]. Also the homogeneity of the protein of interest in inclusion bodies helps in decreasing the number of purification steps to recover the pure protein [Panda, A. K. *Adv. Biochem. Engg./Biotechnol.* 85:43-93 (2003)]. The inclusion body protein also minimizes the toxic effects of the expressed recombinant protein to *E. coli* cells [Lee, J. et al., *Biochem. Biophys. Res. Commun.,* 277:575-580 (2000); Lee, J. et al, *Appl. Microbiol. Biotechnol.,* 58:790-796 (2002); Wei, Q. et al., *Appl. Environ. Microbiol.,* 71(9):5038-5043 (2005); Rao, X. C. et al., *Protein Expr. Purif,* 36:11-18 (2004)]. Overall, the expression of target protein in the form of inclusion bodies ensures that the target protein is produced economically []; Fahnert, B. et al., *Adv. Biochem Engg./Biotechnol.* 89:93-142 (2004); Walsh, G. *Nat. Biotechnol.* 21:865-870 (2003); Mukhopadhyay, A. *Adv. Biochem. Engg./Biotechnol.* 56:61-109 (1997)].

In fact many major biotech companies have been using fusion proteins to express therapeutic peptides in the form of inclusion bodies. In EP 0055945, Genentech reports the use of TrpE and B-galactosidase (lacZ) as a fusion partner to express proinsulin, which is later cleaved off using cyanogen bromide. In EP0211299 A, Hoechst AG, describes the use of D peptide of *E. coli* Trp gene as a fusion partner to express fusion peptides proinsulin and hirudin. In U.S. Pat. No. 5,670,340, Suntory Ltd, Osaka, Japan, reports the use of a fragment of beta galactosidase as a fusion partner along with a leader peptide linked with human calcitonin to express the fusion product as inclusion bodies, where calcitonin is cleaved off using V8 protease after expression. In U.S. Pat. No. 6,500,647, Mogam Biotechnology Institute, exemplified the production of human PTH as inclusion bodies by fusing it to a phosphoribulokinase gene fragment of *Rhodobacter sphaeroides* or its mutated gene as a fusion partner where the fusion product is also containing a urokinase-specific cleavage site. [Wingender, E. et al., *J. Biol. Chem.* 264(8):4367-4373 (1989)] describes the use of variable sizes of cro-beta galactosidase as a fusion partner with PTH which is later cleaved off using acid hydrolysis. Despite the above described successes associated with the use of fusion partners for the production of therapeutic peptides, literature sites a number of problems that still exist with this technology. Some of the examples below illustrate these problems and support the need for inventing better fusion partners.

Not all fusion partners form stable inclusion bodies. Shen [Shen, S-H. *PNAS,* 81:4627-4631 (1984)], describes the bacterial expression of proinsulin using an 80 a.a. long, amino-terminus fragment of β-galactosidase as a fusion partner. This fusion partner resulted in extremely unstable expression of the fusion product not detectable in SDS-PAGE. Stable expression in the form of inclusion bodies was obtained only when two tandem copies of pro-insulin gene were used in conjunction with the above described fusion partner. Therefore an ideal size of the fusion partner appears to be an important criteria for the formation of inclusion bodies.

While often the formation of inclusion bodies is a consequence of high expression rates [Kane, J. F. and Hartley, D. L. *Trends Biotechnol.* 6:95-101 (1988); Fahnert, B. et al., *Adv. Biochem Engg./Biotechnol.* 89:93-142 (2004)], the literature teaches us that such a correlation is not always correct. Mac [Mac, T-T. *Towards solid-state NMR spectroscopic studies of the ETBR/ET-1 complex.* Ph.D. Thesis (2007), Freie Universitat Berlin] used thioredoxin as a fusion partner for the expression of BigET-1 peptide with the intention that the small size of thioredoxin (12 kDa) and its solubility in *E. coli* will ensure a soluble fusion product. In contrast to this expectation, the fusion product formed inclusion bodies but at very poor expression levels (45 mg/L). When GST was used a fusion protein for the expression of ET-1 in the form of inclusion bodies, expression levels of the fusion product increased but still remained in mg/L levels only. Use of beta-galactosidase fragments as a fusion partner also led to the expression of ET-1 in the form of inclusion bodies but the expression levels remained low, yielding only few mg/L quantities of ET-1 at the end of the process [Ohashi, H. et at., *Appl. Microbiol. Biotechnol.* 41:677-683 (1994); Yasufuku, K. et al., *J. Biochem.* 112:360-365 (1992)]. Therefore just the ability of a fusion partner to induce inclusion bodies does not ensure high expression and subsequent commercial viability.

The vast numbers of above references indicate that the production of small peptides from bacteria has been problematic for a variety of reasons. While the problem of proteolysis of peptides in microbial cells is usually taken care of quite successfully by expressing them as fusion proteins but making these processes commercially feasible has been fraught with numerous challenges. While expressing peptides as insoluble fusion proteins is a preferred method of commercial production of peptides by recombinant methods, the choice of a fusion partner is not straight forward. The previously reported fusion proteins do not always behave in a predictable fashion as far as formation of inclusion bodies and/or high and stable expression is concerned. Further, many of them are either not very easily available through commercial sources or their use for commercial production of a desired peptide has not been fully established. Hence there has been a long felt need in the art for a suitable expression system that comprises a fusion partner that would consistently give stable and high expression with a variety of peptides and at a low cost. With this view, the object of the present invention is to develop an expression system comprising such a fusion partner and establish a production method for the production of peptides at a high yield and production efficiency which is equal to or better than those of the existing processes.

The present invention discloses a novel expression system that utilizes a novel fusion partner, G-CSF, which can be consistently used for the high expression of peptides in the form of inclusion bodies. The peptides of interest that can be expressed with this fusion partner, vary not only in their amino acid content but also in their chain length, and are separated from the fusion partner after cleaving the cleavage site, which is pre-designed into the fusion product. The fusion peptide obtained as such, may then be purified using the standard downstream purification methods. The process of production utilizing such an expression system was found to be highly scalable and facilitated in the stable high expression for three peptides that it was tested with.

DESCRIPTION OF FIGURES

FIG. 1 depicts the expression of three fusion products namely, proinsulin, angiotensin and PTH in both uninduced and IPTG-induced cultures of *E. coli* transformed with the expression vectors encoding the said fusion products.

OBJECTS OF INVENTION

The present invention, in one aspect, provides a process for the production of peptides comprising the use of GCSF or its suitable variants as a fusion partner. In an embodiment is provided a process for the expression of peptides as a fusion product using a novel fusion partner, G-CSF or its suitable variants. In another aspect of the invention is provided a novel fusion partner, G-CSF, for the expression of peptides as fusion products.

In another aspect it provides novel fusion products comprising G-CSF linked to the peptides of interest through a cleavage site which can optionally, where appropriate, be through suitable linker that acts as the cleavage site for chemical and/or enzymatic cleavage agents. In another aspect it provides nucleotide constructs encoding the above novel fusion products. In yet another aspect it provides the expression vectors comprising the above nucleotide constructs In yet another aspect it provides the expression systems comprising the above expression vectors.

In another aspect, it provides methods of construction of such expression vectors encoding such fusion product constructs.

In yet another aspect, it provides the methods of construction of expression systems for the high level expression of peptides as fusion products.

In a still further aspect it provides the use of such expression systems comprising the novel fusion product constructs for the high level expression of peptides.

In a specific embodiment is provided method of expressing desired peptides using the fusion partner and expression system of the present invention. Suitable peptides of interest may include but are not limited to peptides of about 10-90 a.a. residues in length. Examples of such peptides include but are not limited to PTH and its analogues, Insulin and its analogues, Calcitonin and its analogues, peptides of the Angiotensin class, and the like, and such peptides including their short chain peptide variants which act similarly.

SUMMARY

The present invention provides a process for producing recombinant peptides of a large range of sizes & therapeutic classes by employing a novel fusion partner, G-CSF. Preferably, these peptides are linked to G-CSF at its C terminus via a chemical or enzymatic cleavage site. This novel expression system utilizes the biosynthetic machinery of the *E. coli* host cell and provides expression of such fusion peptides preferably in the form of insoluble aggregates of the fusion product in the transformed host cells. The inclusion bodies can be easily isolated from the host cells, and from which, the peptide purified using standard protein purification methodology after cleaving it from the fusion partner, G-CSF by known techniques.

DESCRIPTION OF THE INVENTION

The present invention provides an expression system for the production of peptides in the host cell, where the desired peptide is operatively linked with the fusion partner. The linking or connection is done through an creation of an appropriate cleavage site, thereby forming a complete fusion product. Preferably, the fusion products are insoluble aggregates.

Fusion Partner

The novel expression systems described in this invention comprise of a fusion partner, G-CSF (Genbank Accession number, gi:27437050), which is fused with a suitable peptide to form the fusion protein. Suitable mutants and variants of G-CSF are also contemplated & included as fusion partners as long as they perform the same function of G-CSF. A preferred advantage of the fusion protein is that it provides high level of expression of the said peptide. More specifically, the fusion partner of the present invention is methionyl human GCSF (Sequence ID No 1).

Fused Peptide

The fused peptide is the peptide which is expressed along with the fusion partner in the form of a single fusion product construct. The fused peptide may have several forms. It includes a natural peptide of interest and/or any of its mutants or variants, and/or may include new peptides not found in nature and which is completely designed by man.

Preferably, the peptides are selected from those having from about 10-90 amino acid length. In one embodiment, a fused peptide may be selected from, caltrin, calcitonin, insulin, angiotensin, tissue plasminogen activator, growth hormones, growth factors, growth hormone releasing factors, erythropoietin, interferons, interleukins, oxytocin, vasopressin, ACTH, collagen binding protein, parathyroid hormones, glucagon like peptides, glucagons, proinsulin, tumor necrosis factors, substance P, brain naturetic peptide, individual heavy and light antibody chains, fuzeon, octreotide, somatostatin and the variants including mutants, synthetic analogs and mimetics of these peptides. In a preferred embodiment of the present invention are provided fused peptides that include, PTH, angiotensin and proinsulin. As examples of preferred Embodiments are provided fused peptides which comprise the amino acid sequence of PTH (1-34) (SEQ ID NO:6 and SEQ ID NO:7), Angiotension (SEQ ID NO:17) and Proinsulin (SEQ ID NO:13).

Fusion Product or Fusion Product Construct—

The fusion product construct of the present invention is represented by the formula Fusion partner-CS-Fusion peptide wherein a fusion peptide of interest is a physiologically active peptide, CS is a cleavage site either present within the fusion partner or the fusion peptide amino acid (a.a.) sequences or is a suitable linker of a suitable length of a.a, residues, and the fusion partner is GCSF or its variants.

The preferred fusion product or the fusion product construct contemplated in this invention may have the following formulae:

N-terminal Fusion Partner-CS-Peptide of interest
C-terminal

N-terminal Peptide of interest-CS-Fusion Partner
C-terminal

In a more preferred embodiment of the present invention a fusion product of the following formula is contemplated:

N-terminal Peptide of interest-CS-Fusion Partner
C-terminal wherein CS represents an enzymatic or chemical cleavage site. As preferred embodiments of the present invention fusion proteins of the following formulae are contemplated:

G-CSF-Enterokinase cleavage site-PTH (G-CSF-
PTH), (SEQ ID NO:7)

wG-CSF-CNBr cleavage site-Proinsulin (G-CSF-Proinsulin), (SEQ ID NO:13)

G-CSF-Enterokinase cleavage site-Angiotensin
(G-CSF-Angiotensin), (SEQ ID NO:17).

Cleavage Site

The cleavage sites contemplated in the above invention comprise chemical cleavage sites such as those cleavable by cynogen bromide or 2-(2-nitrophenylsulphenyl)-methyl-3'-bromoindolenine, BNPS-skatole (3-bromo-3-methyl-2-(2-nitrophenyl)thiol-3H-indole), N-bromosuccinamide, O-iodosobenzoic acid, HBr/DMSO, NTCB (2-Nitro-5-thiocyanobenzoate), Sodium metal in liquid ammonia, Hydroxylamine, dilute acid for acid hydrolysis, and the like; or enzymatic cleavage sites such as those recognized by Enterokinase, Trypsin, Chymotrypsin, Elastase, Pepsin, Papain, Subtilisin, Thermolysin, V8 Protease, Endoproteinase Arg C (submaxillaris protease), Clostripain, Thrombin, Collagenase, Lysobacter enzymogenes (Lys C), Mysobacter A1-1 Protease, Factor Xa, and the like. The cleavage site is inserted by using standard molecular biology techniques such as the polymerase chain reaction where the reaction is carried out using one or both of the above genes (peptide and fusion partner) as templates and mutated oligos capable of introducing the said sites as primers of the reaction. Alternatively, the cleavage site may also exist naturally within the peptide or fusion partner.

Expression Vector

An expression vector is a suitable plasmid vector that comprises an expression cassette encoding the gene for such a fusion product or fusion product construct as the one described above wherein the expression cassette is operably linked to a suitable promoter and other suitable regulatory elements functional in the expression host into which the expression vector has been transformed or transfected for the expression of such fusion product. Examples of expression vectors include those vectors which can express the fusion product in *E. coli*. Examples of such expression vectors may be pET27, pET11, pET3, pET32 and the like which use the T7 promoter system, pBAD or pARA (Invitrogen) series of vectors based on the arabinose operon and AraC activator. Other examples include the vectors containing lambda PL promoters such as pGW7, a pBR322 based vector containing the lambda PL promoter, PL vector series (invitrogen) inducible by temperature shift to 42 deg C., or other plasmid vectors designed to contain the lac, lacUV5, tac, trc (IPTG inducible), trp(Tryptophan), araBAD (Arabinose), phoA (phosphate starvation), cst-1 (glucose starvation), cspA (cold inducible), SP6, T3 promoter to give expression in *E. coli*.

Expression System

The expression of a foreign protein by interaction of the recombinant expression vectors encoding the gene for the said protein with the biosynthetic machinery of the host cells is a well known technique for the biochemical synthesis of proteins. By the term, "Expression system", is meant an expression vector that encodes the gene for such a fusion product or fusion product construct as the one described above, and the transformed *E. coli* host cell, in which the fusion product is produced.

In the present invention, the *E. coli* expression system utilized for the expression of the peptide of interest comprises an expression vector, in which the desired peptide is operatively linked with the fusion partner, G-CSF, in any order, with either the peptide, or the fusion partner, at the C-terminus, with a cleavage site in between the two units. Preferentially, the peptide is encoded at the C-terminus of G-CSF. An example of the preferred expression vector is pET27B-GCSF-PTH, which encodes for a fusion product, G-CSF-PTH (1-34). *E. coli* DH5α transformed with the above vector have been deposited as pET-GFL-PTH$^{1-34}$ cells, at Microbial Type Culture Collection and Gene Bank, Institute of Microbial Technology, India, under the accession number MTCC 5425. Another preferred example of such an expression vector is pET27B-GCSF-Proinsulin, which encodes for a fusion product, G-CSF-Proinsulin. *E. coli* DH5α transformed with the above vector have been deposited as pET-GFL-Proinsulin cells, at Microbial Type Culture Collection and Gene Bank, Institute of Microbial Technology, India, under the accession number MTCC 5424.

An *E. coli* cell which has been produced after transformation by an expression vector such as the one described above, and that expresses the peptide of interest as a fusion product, is also a part of the present invention. In a preferred embodiment of this aspect of the invention, the transformed cell has been obtained by transforming BL21 (DE3) strain of *E. coli*.

The expression system described in this invention may be used for the expression of any peptide in form of a fusion product with G-CSF as a fusion partner. Preferentially, the length of the peptide varies from 10-86 a.a. residues.

Production of Peptide in the Host Cell

For the production of the peptide in the form of a fusion product the host cells are transformed with an expression vector encoding the previously contemplated fusion product construct. The expression vector may be derived from any base vector that is compatible with the host of interest by cloning the DNA segment encoding the fusion product into the base vector under the control of an appropriate host-compatible promoter. Besides the promoter, the base vector may also consist of other host-compatible regulatory elements such as those involved in the regulation of transcription and translation of the gene product. In general the choice of the base vector and the regulatory elements therein is based upon the compatibility of the vector with the host to obtain high expression of the fusion product. The host cell contemplated in the invention may be any microbial host cell that tends to form inclusion bodies upon high expression of protein inside the cell. In one preferred embodiment of the invention, the microbial host cell is *E. coli*.

Typically, the recombinant gene inserted into an appropriate base vector which is used to transform the host cells leads to the expression inside the transformed host cell of the fusion product as either a soluble product or as an insoluble product. In the present invention the preferred form of expression of the fusion product is in the form of insoluble product that results in the formation of inclusion bodies. The peptides can be selected from those described above and elsewhere in the specification. In particular, the fusion product comprises a single copy of the peptide of interest that is selected from the group comprising of PTH (1-34), (SEQ ID NO:6 and SEQ ID NO:7) Angiotension (SEQ ID NO:17) and Proinsulin (SEQ ID NO:13) and that is expressed as inclusion bodies in an *E. coli* host cell.

One of the examples of high expression of peptide described in the invention is the use of the expression systems of the invention to express high levels of PTH. The Human PTH (1-34) gene was synthesised by first annealing with each other, the two complementary oligonucleotides which were designed on the basis of the sequence of the Parathyroid hormone, and then by carrying out the polymerase chain reaction to fill the remaining gaps. Subsequently, the enzyme cleavage site and the 5'- and 3'-end restriction enzyme sites were incorporated into the gene by another PCR reaction using specific primers. This modified-PTH gene which now carries the enzyme cleavage site at its 5'-end and also carried the necessary restriction enzyme sites at both its ends, was further cloned into the pET vector already containing the GCSF gene. This cloning was done in such a manner so that the fusion product expressed by the cell transformed by it would comprise of the G-CSF a.a. sequence, followed by the enzyme cleavage site, further followed by the PTH (1-34) a.a. sequence as a single fusion product.

One of the preferred expression systems contemplated in the above described invention comprises the expression of a fusion product consisting of G-CSF and PTH separated by an enterokinase cleavage site. Another expression system contemplated in this invention comprises the expression of a fusion product consisting of G-CSF and proinsulin separated by a CNBr cleavage site. A still another preferred expression system contemplated in this invention comprises the expression of a fusion product consisting of G-CSF and angiotensin separated by the enterokinase cleavage site.

The above peptides of interest may be produced in an industrially feasible manner as insoluble fusion products forming inclusion bodies in the *E. coli* host using standard fermentation methods as described in the literature. A single colony of the recombinant *E. coli*, harboring an expression vector encoding the desired fusion product is transferred to 5-mL Kanamycin-containing (50 mg/L) Luria Bertani medium. The culture is grown at 37° C. for 12-15 h at 200 rpm. The broth is used to inoculate 100-mL of the Kanamycin-containing (50 mg/L) Luria Bertani medium. The culture is sub-cultured to get about 1 L broth, which is used to inoculate 10-L culture medium in a fermenter. The growth phase of fermentation is carried out either in a batch or a fed-batch manner. The composition of batch and fed-batch feed media are as follows:

Composition of Batch Media:

| Component | Concentration (1/L) |
|---|---|
| KH$_2$PO$_4$ | 13.3 g |
| (NH$_4$)$_2$HPO$_4$ | 4.0 g |
| Yeast extract | 1.0 g |
| Glucose | 20.0 g |
| Citric acid | 1.7 g |
| MgSO$_4$7H$_2$O | 1.2 g |
| Trace metal solution | 20 ml |
| Kanamycin | 50 mg |

Composition of Fed-Batch Feed Media:

| Component | Concentration (1/L) |
|---|---|
| Glucose | 700 g |
| MgSO$_4$•7H$_2$O | 20 g |
| Kanamycin | 500 mg |
| Trace metal solution | 20 ml |

The fermentation is carried out at 37° C., pH 6.8-7.0, 30-70% dissolved oxygen, with agitation. The feed-media is added either continuously or discontinuously. After attaining sufficient optical density (30-100 AU at 600 nm) the gene expression is induced by the addition of IPTG (0.1-2 mM) into the culture broth, thereby starting the production phase. The production phase is carried out either in batch, or fed-batch or repeated fed-batch mode. After the sufficient expression of protein in the form of inclusion bodies, the batch is harvested and centrifuged. The cell paste, obtained from the broth, is transferred for downstream processing The inclusion bodies containing the fusion product comprising of the peptide and the fusion partner, are isolated from the *E. coli*. cells by disruption using any of the suitable methods reported in the literature. The fusion product is solubilized from the isolated inclusion bodies using any of the standard methods reported in the literature. The desired peptide is separated from the fusion partner by treating it with an appropriate cleavage molecule, i.e., enzyme or chemical agent. The peptide of interest is then obtained from this mixture and brought to a high level of purity and yield by using standard methods of purification such as precipitation, column chromatography etc. reported extensively in the literature. The order of cleavage within the various downstream steps and the number and type of purification methods used in the invention may follow any of the suitable protocols reported in the standard literature. The expression systems of this invention may be used to produce high level of expression of other peptides as well, e.g., insulin, calcitonin, exendin and the like. The invention is described in further details through the following examples which teach the skilled person to carry out the present invention. It will be appreciated that these examples are illustrative and the skilled person, following the teachings of these examples, which are for specific peptides, replicate the teachings with suitable modifications, alterations etc. as may be necessary, and which are within the scope of a skilled person, for other peptides which have been contemplated to be within the scope of the present invention.

EXAMPLE 1

Construction of GCSF Expression Vector

Human placental total RNA (Clontech) was used as a template for reverse transcriptase-polymerase chain reaction (RT-PCR) based cloning of the desired GCSF (174 amino acid variant) gene sequence. PCR was performed using a pair of gene specific oligonucleotide primers (SEQ ID NO:3 and SEQ ID NO:4). The oligonucleotides also contained the cloning sites and the start codon for Methionine, and were designed to modify the 5' end of the gene such that the GC content of the 5' region was reduced without affecting the amino acid sequence and the optimized codons were also efficiently used by *E. coli*. Seven codons were modified at 5' end. Double stranded cDNA was synthesized from Human placental total RNA using MMLV reverse transcriptase (MBI Fermentas, USA) by gene specific priming [Maniatis et al., Molecular cloning; A Laboratory Manual (Cold Spring harbor Laboratory Press, Cold Spring Harbor, N.Y.), (1990)]. This cDNA was then subjected to 40 cycles of PCR amplification using 100 picomoles of gene specific oligonucleotide primers in a volume of 100 µl containing 50 mM Tris-Cl (pH8.3), 2.5 mM $MgCl_2$, 200 µM each of the 4 dNTPs and 2.5 units of Pfu Polymerase. Each PCR amplification cycle consisted of incubations at 94° C. for 30 sec (denaturation), 61° C. for 30 sec (annealing) and 72° C. for 1 min (extension). This amplified PCR product was cleaned using Gel extraction Kit (Qiagen) and was digested with Nde I and Bam HI restriction endonucleases. The digested PCR product was further purified using Gel Extraction kit (Qiagen). The plasmid vector pET27b(+), (Novagen) was digested using Nde I and Bam HI restriction endonucleases and subsequently the linearized plasmid vector was gel purified using Gel extraction kit (Qiagen). This purified linearized vector DNA was ligated with the purified GCSF PCR product digested with Nde I and Bam HI. The ligation product was transformed in E. coli DH5a and transformants were scored on the basis of Ampicillin resistance. Plasmid DNA isolated from such 10 colonies was analysed for the presence of GCSF gene by restriction digestion using various restriction enzymes. One such plasmid was sequenced using automated DNA sequencer (ABI) and found to be having the correct integration and sequence of the protein gene. This plasmid DNA was named pET27b(+)-GCSF-1. This plasmid DNA was transformed in E. coli BL21 DE3 competent cells by $CaCl_2$ chemical transformation method to obtain the G-CSF expressing E. coli cell clones. One such E. coli clone was earlier used to obtain very high expression levels of up to 9.5 g/L using a fermentation process described in WO 2007/102174 A2.

EXAMPLE 2

Construction of PTH Fusion Protein Expression Vector.

Human GCSF gene was PCR amplified from pET27b(+)-GCSF-1 plasmid vector prepared earlier, using a set of oligonucleotide primers where the forward primer contained the restriction site Nde I (SEQ ID NO:3), and reverse primer contained a BamHI restriction enzyme site (SEQ ID NO:51. This amplified PCR product was cleaned using Gel extraction Kit (Qiagen) and was digested with Nde I and Bam HI restriction endonucleases. The digested PCR product was further purified using Gel Extraction kit (Qiagen).

Human Parathyroid Hormone (1-34) gene was synthesised using two complementary oligonucleotides (SEQ ID NO:8 and SEQ ID NO:9) corresponding to the coding and anticoding strand of the Human Parathyroid Hormone (1-34) gene. Equimolar concentrations of both the oligonucleoties were heated in a Thermal Cycler at 95 degree celcius for 5 minutes and then allowed to anneal by cooling at room temperature for an hour. The annealed oligonucleotides were then subjected to 40 cycles of PCR amplification using 100 picomoles of gene specific oligonucleotide forward and reverse primers (SEQ ID NO:10 and SEQ ID NO:11) in a volume of 100 µl, containing 50 mM Tris-Cl (pH8.3), 2.5 mM $MgCl_2$, 200 µM each of the 4 dNTPs and 2.5 units of Pfu Polymerase. Each PCR amplification cycle consisted of incubations at 94° C. for 30 sec (denaturation), 62° C. for 30 sec (annealing) and 72° C. for 1 min (extension). The forward primer contained the BamHI restriction site along with the Enterokinase Cleavage site. The amplified product of the PCR reaction was resolved on a 2.5% Agarose gel and was purified using Gel Extraction kit (Qiagen) The isolated PTH gene was digested using BamHI and Bpu1102 I restriction endonucleases and subsequently purified using gel extraction kit (Qiagen).

The plasmid vector pET27 b (+), (Novagen) was digested using Nde I and Bpu1102I restriction endonucleases and subsequently the linearized plasmid vector was gel purified using Gel extraction kit (Qiagen).

Ligation of the linearized vector with GCSF and PTH (1-34) gene fragments was carried out in a 3 fragment ligation reaction. The ligation mix was transformed in E. coli DH5 α-FT and plated on LB containing kanamycin. The colonies were screened using various restriction enzymes. The sequence was further confirmed by sequencing using automated DNA sequencer (ABI) and found to be having the correct integration and sequence of the HuGCSF-PTH (1-34) fusion protein gene (SEQ ID NO:6 and SEQ ID NO:7). This plasmid clone was named pET27b-GCSF-PTH (1-34).

EXAMPLE 3

Construction of Proinsulin Fusion Protein Expression Vector

Human pancreatic total RNA (Clontech) was used as a template for reverse transcriptase-polymerase chain reaction (RT-PCR) based cloning of the desired proinsulin gene sequence. PCR was performed using a pair of gene specific oligonucleotide forward and reverse primers (SEQ ID NO:14 and SEQ ID NO:15) corresponding to the coding region of the Proinsulin gene (SEQ ID NO:12 and SEQ ID NO:13). Double stranded cDNA was synthesized from Human placental total RNA using MMLV reverse transcriptase (MBI Fermentas, USA) by gene specific priming [Maniatis et al., Molecular cloning; A Laboratory Manual (Cold Spring harbor Laboratory Press, Cold Spring Harbor, N.Y.), (1990)]. This cDNA was then subjected to 40 cycles of PCR amplification using 100 picomoles of gene specific oligonucleotide primers in a volume of 100 µl containing 50 mM Tris-Cl (pH8.3), 2.5 mM $MgCl_2$, 200 µM each of the 4 dNTPs and 2.5 units of Pfu Polymerase. Each PCR amplification cycle consisted of incubations at 94° C. for 30 sec (denaturation), 58° C. for 30 sec (annealing) and 72° C. for 1 min (extension). Amplified product of the PCR reaction was resolved on a 1.5% Agarose gel. The desired fragment of approximately 280 base pairs in size was excised out from the gel and purified using Qiagen Gel extraction kit. This purified DNA fragment was ligated into pET27b-GCSF-PTH (1-34) after restriction digestion of both the vector and the purified PCR product with BamHI and Bpu1102I (MBI Fermentas, USA). The digestion of the vector construct with BamHI and Bpu1102I excised the PTH (1-34) gene from the construct and the digested expression vector was purified using Qiagen Gel extraction kit. Purified vector was used for ligation with the digested and purified Proinsulin PCR product. The ligation product was transformed in E. coli DH5α and transformants were scored on the basis of Kanamycin resistance. Plasmid DNA isolated from such 10 colonies was analysed for the presence of Proinsulin gene by restriction digestion using various restriction enzymes. One such plasmid was sequenced using automated DNA sequencer (ABI) and found to be having the correct integration and sequence of the Hu-GCSF-Proinsulin fusion protein (SEQ ID NO:17). This plasmid DNA was named pET27B-GCSF-Proinsulin.

EXAMPLE 4

Construction of Angiotensin (1-10) Fusion Protein Expression Vector

The gene encoding the Angiotensin fusion protein was constructed by using pET27b-GCSF-PTH vector construct as a template in a PCR reaction using oligonucleotide forward and reverse primers of (SEQ ID NO:18 and SEQ ID NO:19), where the forward primer had complementarity to the upstream region of the vector and the reverse primer contained the Enterokinase cleavage site and the Angiotensin (1-10) anticoding region and had complementarity to the 3' end of G-CSF, such that the PCR product of the reaction was the coding sequence for the G-CSF-Enterokinase-Angiotensin fusion product (SEQ ID NO:12). The PCR reaction was carried out for 40 cycles of PCR amplification using 100 picomoles of gene specific oligonucleotide primers in a volume of 100 μl containing 50 mM Tris-Cl (pH8.3), 2.5 mM $MgCl_2$, 200 μM each of the 4 dNTPs and 2.5 units of Pfu Polymerase. Each PCR amplification cycle consisted of incubations at 94° C. for 30 sec (denaturation), 55° C. for 30 sec (annealing) and 72° C. for 1 min (extension). Amplified product of the PCR reaction was resolved on a 1% Agarose gel. The desired fragment of approx 600 base pairs in size was excised out from the gel and purified using Qiagen Gel extraction kit. This purified DNA fragment was ligated into pET27b after restriction digestion of both the vector and the purified PCR product with XbaI and Bpu1102I (MBI Fermentas, USA). The ligation product was transformed in E. coli DH5α and transformants were scored on the basis of Kanamycin resistance. Plasmid DNA isolated from such 10 colonies was analysed for the presence of GCSF-Angiotensin fusion protein gene by restriction digestion using various restriction enzymes. One such plasmid was sequenced using automated DNA sequencer (ABI) and found to be having the correct integration and sequence of the fusion protein. This plasmid DNA was named pET27b-GCSF-angiotensin.

EXAMPLE 5

Expression Analysis of the Fusion Protein Constructs.

All the three fusion protein expression vector constructs described above were extracted from their respective E. coli DH5α hosts described above and re-transformed into E. coli BL21 (DE3) using $CaCl_2$ chemical transformation method. Individual colonies from each set were inoculated in LB broth containing kanamycin (50 mg/L). On reaching an $OD_{600}$ of 0.8, the cultures were induced using 2 mM IPTG. The cells were harvested after 16 Hrs of induction. 25 μl cell suspension was lysed in the presence of SDS and beta mercapto ethanol (Gel loading buffer) and it was loaded on 15% SDS PAGE and the induced protein band was quantitated using densitometry (Image quant 400, image quant TL ver 2005, 1D gel analysis.).

FIG. 1 shows the picture of gels showing the various fusion products in uninduced and induced cultures. Densitometric analysis of these gels showed that GCSF-PTH fusion protein accumulated in the cultures at a very high expression level of 55.56% of total bacterial protein. GCSF-Proinsulin fusion protein was also expressed at high levels of 40% of total bacterial protein. The small peptide of 10 amino acids, angiotensin, when expressed as a GCSF-Angiotensin fusion product, was also produced at a high expression level of 50.28% of total bacterial protein. The proinsulin and PTH fusion proteins clones were tested for the presence of the induced protein in soluble or insoluble form. The cells were lysed by high pressure cell homogenizer and the insoluble inclusion bodies were centrifuged and separated and solubilized. The solubilized inclusion bodies and the supernatant were both analysed by gel electrophoresis. More than 90% of the induced protein was found to be present in the form of insoluble inclusion bodies.

EXAMPLE 6

Expression of PTH Fusion Protein in Fermenter

Using the expression systems of this invention, the recombinant PTH fusion protein, could be produced in fermenters in an industrially feasible manner. A single colony of the recombinant E. coli BL21 (DE3), harboring the PTH fusion protein expression vector was transferred to 5-mL Kanamycin-containing (50 mg/L) Luria Bertani medium. The culture was grown at 37° C. for 12-15 h at 200 rpm. The broth was used to inoculate 100-mL of the Kanamycin-containing (50 mg/L) Luria Bertani medium. The culture was sub-cultured to get about 1 L broth, which was used to inoculate 10-L culture medium in a 30-L fermenter. The growth phase of fermentation can be carried out in batch or fed-batch manner and the composition of batch and fed-batch feed media are given below. Specifically in this example we carried out the growth phase of fermentation in the fed-batch mode.

Composition of Batch Media:

| Component | Concentration (1/L) |
|---|---|
| $KH_2PO_4$ | 13.3 g |
| $(NH_4)_2HPO_4$ | 4.0 g |
| Yeast extract | 1.0 g |
| Glucose | 20.0 g |
| Citric acid | 1.7 g |
| $MgSO_4 \cdot 7H_2O$ | 1.2 g |
| Thiamine | 0.1 g |
| Trace metal solution | 20 ml |
| Kanamycin | 50 mg |

Composition of Fed-Batch Feed Media:

| Component | Concentration (1/L) |
|---|---|
| Glucose | 700 g |
| $MgSO_4 \cdot 7H_2O$ | 20 g |
| Kanamycin | 500 mg |
| Trace metal solution | 20 ml |

The fermentation was carried out at 37° C., pH 6.8-7.0, 30-70% dissolved oxygen, with agitation. The feed-media can be added continuously or discontinuously. Specifically in this example, the feed-batch media was added continuously in a substrate-limiting fed-batch manner. After attaining sufficient optical density (30-100 AU at 600 nm) the gene expression was induced by addition of IPTG (0.1-2 mM) into the culture broth, thereby starting the production phase. The production phase can be carried out in batch, fed-batch or repeated fed-batch mode. Specifically in this example we carried out the production phase in a fed-batch mode and the composition of the fed-batch media used is given below.

Composition of Fed-Batch Feed Media for Production Phase:

| Component | Concentration (1/L) |
|---|---|
| Glucose | 270 g |
| Yeast extract | 214 g |
| $MgSO4 \cdot 7H_2O$ | 1 g |
| Kanamycin | 500 mg |

The production phase was carried out for a period of 12 hours using continuous addition of fed-batch media for production phase and was added in a substrate-limiting fed-batch manner. After the sufficient expression of protein the batch is harvested and centrifuged. The cell paste, obtained from the broth, is transferred for downstream processing. The volumetric yield of the PTH fusion protein was measured by densitometric analysis of SDS-PAGE gels, and determined to be 4.62 g/L.

EXAMPLE 7

Expression of Pro-Insulin Fusion Protein in Fermenter

Using the expression systems of this invention, the recombinant Pro-insulin fusion protein, could be produced in fermenters in an industrially feasible manner. A single colony of the recombinant *E. coli* BL21 (DE3), harboring the Pro-insulin fusion protein expression vector was transferred to 5-mL Kanamycin-containing (50 mg/L) Luria Bertani medium. The culture was grown at 37° C. for 12-15 h at 200 rpm. The broth was used to inoculate 100-mL of the Kanamycin-containing (50 mg/L) Luria Bertani medium. The culture was sub-cultured to get about 1 L broth, which was used to inoculate 10-L culture medium in a 30-L fermenter. The growth phase of fermentation can be carried out in batch or fed-batch manner and the composition of batch and fed-batch feed media are given below. Specifically in this example we carried out the growth phase of fermentation in the fed-batch mode.

Composition of Batch Media:

| Component | Concentration (1/L) |
|---|---|
| $KH_2PO_4$ | 13.3 g |
| $(NH_4)_2HPO_4$ | 4.0 g |
| Yeast extract | 1.0 g |
| Glucose | 20.0 g |
| Citric acid | 1.7 g |
| $MgSO_4 7H_2O$ | 1.2 g |
| Thiamine | 0.1 g |
| Trace metal solution | 20 ml |
| Thiamine | 0.1 g |
| Trace metal solution | 20 ml |
| Kanamycin | 50 mg |

Composition of Fed-Batch Feed Media:

| Component | Concentration (1/L) |
|---|---|
| Glucose | 700 g |
| $MgSO_4 \cdot 7H_2O$ | 20 g |
| Trace metal solution | 20 ml |

The fermentation was carried out at 37° C., pH 6.8-7.0, 30-70% dissolved oxygen, with agitation. The feed-media can be added continuously or discontinuously. After attaining sufficient optical density (30-100 AU at 600 nm) the gene expression was induced by addition of IPTG (0.1-2 mM) into the culture broth, thereby starting the production phase. The production phase can be carried out in batch, fed-batch or repeated fed-batch mode. Specifically in this example we carried out the production phase in a fed-batch mode and the composition of the fed-batch media used is given below.

Composition of Fed-Batch Feed Media for Production Phase:

| Component | Concentration (1/L) |
|---|---|
| Glucose | 270 g |
| Yeast extract | 214 g |
| $MgSO_4 \cdot 7H_2O$ | 1 g |

Kanamycin (20-450 mg/L) was added after a suitable period of time (0-12 h) after induction. The production phase was carried out for a period of 12 hours using continuous addition of fed-batch media for production phase and was added in a substrate-limiting fed-batch manner. After the sufficient expression of protein the batch is harvested and centrifuged. The cell paste, obtained from the broth, is transferred for downstream processing. The volumetric yield of fusion proinsulin, measured by densitometric analysis of SDS-PAGE gels, was determined to be 3.38 g/L.

The sequences of the protein, nucleotides and oligonucleotides (Seq IDs Nos. 1 to 19) are as follows:

```
INFORMATION FOR SEQ ID NO 1 and 2:
(i)   SEQUENCE CHARACTERISTICS:
(A)   LENGTH: 528 bases (B)   TYPE: Nucleic acid and amino acid (C)   STRANDEDNESS: single (D)   TOPOLOGY: linear (ii)  FEATURE
(A)   NAME/KEY: CDS (Methionyl Human GCSF coding sequence and protein)

(B)   LOCATION: 1-525

SEQ ID NO 1 and 2
    1   ATG ACT CCA TTA GGT CCA GCA AGC TCC CTG CCC CAG AGC TTC CTG        45
    1    M   T   P   L   G   P   A   S   S   L   P   Q   S   F   L        15

46   CTC AAG TGC TTA GAG CAA GTG AGG AAG ATC CAG GGC GAT GGC GCA        90
   16    L   K   C   L   E   Q   V   R   K   I   Q   G   D   G   A        30

91   GCG CTC CAG GAG AAG CTG TGT GCC ACC TAC AAG CTG TGC CAC CCC       135
   31    A   L   Q   E   K   L   C   A   T   Y   K   L   C   H   P        45

136   GAG GAG CTG GTG CTG CTC GGA CAC TCT CTG GGC ATC CCC TGG GCT       180
   46    E   E   L   V   L   L   G   H   S   L   G   I   P   W   A        60
```

```
181 CCC CTG AGC AGC TGC CCC AGC CAG GCC CTG CAG CTG GCA GGC TGC    225
 61  P   L   S   S   C   P   S   Q   A   L   Q   L   A   G   C     75

226 TTG AGC CAA CTC CAT AGC GGC CTT TTC CTC TAC CAG GGG CTC CTG    270
 76  L   S   Q   L   H   S   G   L   F   L   Y   Q   G   L   L     90

271 CAG GCC CTG GAA GGG ATC TCC CCC GAG TTG GGT CCC ACC TTG GAC    315
 91  Q   A   L   E   G   I   S   P   E   L   G   P   T   L   D    105

316 ACA CTG CAG CTG GAC GTC GCC GAC TTT GCC ACC ACC ATC TGG CAG    360
106  T   L   Q   L   D   V   A   D   F   A   T   T   I   W   Q    120

361 CAG ATG GAA GAA CTG GGG ATG GCC CCT GCC CTG CAG CCC ACC CAG    405
121  Q   M   E   E   L   G   M   A   P   A   L   Q   P   T   Q    135

406 GGT GCC ATG CCG GCC TTC GCC TCT GCT TTC CAG CGC CGG GCA GGA    450
136  G   A   M   P   A   F   A   S   A   F   Q   R   R   A   G    150

451 GGG GTC CTA GTT GCC TCC CAT CTG CAG AGC TTC CTG GAG GTG TCG    495
151  G   V   L   V   A   S   H   L   Q   S   F   L   E   V   S    165

496 TAC CGC GTT CTA CGC CAC CTT GCC CAG CCC TGA                   528
166  Y   R   V   L   R   H   L   A   Q   P   *

INFORMATION FOR SEQ ID NO 3:
(i)   SEQUENCE CHARACTERISTICS:
(A)   LENGTH: 23 bases (B)   TYPE: Nucleic acid (oligonucleotide)

(C)   STRANDEDNESS: single (D)   TOPOLOGY: linear

Seq id no 3:
GCGCATATGACTCCATTAGGTCC

INFORMATION FOR SEQ ID NO 4:
(i)   SEQUENCE CHARACTERISTICS:
(A)   LENGTH : 32 bases (B)   TYPE: Nucleic acid (oligonucleotide)

(C)   STRANDEDNESS: single (D)   TOPOLOGY: linear

Seq Id no 4:
GCGGATCCTCAGGGCTGGGCAAGGTGGCGTAG

INFORMATION FOR SEQ ID NO 5:
(i)   SEQUENCE CHARACTERISTICS:
(A)   LENGTH: 29 bases (B)   TYPE: Nucleic acid (oligonucleotide)

(C)   STRANDEDNESS: single (D)   TOPOLOGY: linear

Seq Id no 5:
GCGGATCCGGGCTGGGCAAGGTGGCGTAG

INFORMATION FOR SEQ ID NO 6 and 7:
(i)   SEQUENCE CHARACTERISTICS:
(A)   LENGTH: 651 bases (B)   TYPE: Nucleic acid (C)   STRANDEDNESS: single (D)   TOPOLOGY: linear (ii)  FEATURE
(A)   NAME/KEY: CDS (GCSF-PTH fusion protein)

(B)   LOCATION: 1-648
```

(iii) FEATURE
(A) NAME/KEY: GCSF Fusion partner (B) LOCATION: 1-525

(iv) FEATURE
(A) NAME/KEY: Enterokinase cleavage site (B) LOCATION: 532-546

(v) FEATURE
(A) NAME/KEY: PTH (1-34)

(B) LOCATION: 547-648

```
                                                            SEQ ID NO 6 and 7
  1 ATG ACT CCA TTA GGT CCA GCA AGC TCC CTG CCC CAG AGC TTC CTG         45
  1  M   T   P   L   G   P   A   S   S   L   P   Q   S   F   L         15

46 CTC AAG TGC TTA GAG CAA GTG AGG AAG ATC CAG GGC GAT GGC GCA         90
 16  L   K   C   L   E   Q   V   R   K   I   Q   G   D   G   A         30

91 GCG CTC CAG GAG AAG CTG TGT GCC ACC TAC AAG CTG TGC CAC CCC        135
 31  A   L   Q   E   K   L   C   A   T   Y   K   L   C   H   P         45

136 GAG GAG CTG GTG CTG CTC GGA CAC TCT CTG GGC ATC CCC TGG GCT        180
 46  E   E   L   V   L   L   G   H   S   L   G   I   P   W   A         60

181 CCC CTG AGC AGC TGC CCC AGC CAG GCC CTG CAG CTG GCA GGC TGC        225
 61  P   L   S   S   C   P   S   Q   A   L   Q   L   A   G   C         75

226 TTG AGC CAA CTC CAT AGC GGC CTT TTC CTC TAC CAG GGG CTC CTG        270
 76  L   S   Q   L   H   S   G   L   F   L   Y   Q   G   L   L         90

271 CAG GCC CTG GAA GGG ATC TCC CCC GAG TTG GGT CCC ACC TTG GAC        315
 91  Q   A   L   E   G   I   S   P   E   L   G   P   T   L   D        105

316 ACA CTG CAG CTG GAC GTC GCC GAC TTT GCC ACC ACC ATC TGG CAG        360
106  T   L   Q   L   D   V   A   D   F   A   T   T   I   W   Q        120

361 CAG ATG GAA GAA CTG GGG ATG GCC CCT GCC CTG CAG CCC ACC CAG        405
121  Q   M   E   E   L   G   M   A   P   A   L   Q   P   T   Q        135

406 GGT GCC ATG CCG GCC TTC GCC TCT GCT TTC CAG CGC CGG GCA GGA        450
136  G   A   M   P   A   F   A   S   A   F   Q   R   R   A   G        150

451 GGG GTC CTA GTT GCC TCC CAT CTG CAG AGC TTC CTG GAG GTG TCG        495
151  G   V   L   V   A   S   H   L   Q   S   F   L   E   V   S        165

496 TAC CGC GTT CTA CGC CAC CTT GCC CAG CCC GGA TCC                    540
166  Y   R   V   L   R   H   L   A   Q   P   G   S                    180

541         TCG GTG TCG GAA ATA CAG CTT ATG CAT AAC CTG GGA AAA        585
181          S   V   S   E   I   Q   L   M   H   N   L   G   K        195

586 CAT CTG AAC TCG ATG GAG AGA GTA GAA TGG CTG CGT AAG AAG CTG        630
196  H   L   N   S   M   E   R   V   E   W   L   R   K   K   L        210

631 CAG GAT GTG CAC AAT TTT TAG                                        651
211  Q   D   V   H   N   F   *
```

INFORMATION FOR SEQ ID NO 8:
(i) SEQUENCE CHARACTERISTICS:
(A) LENGTH: 104 bases (B) TYPE: Nucleic acid (oligonucleotide for synthesis for PTH(1-34))

(C) STRANDEDNESS: single (D) TOPOLOGY: linear

Seq id no 8:
CGGTGTCGGAAATACAGCTTATGCATAACCTGGGAAAACATCTGAACTCGATGGAGAG

AGTAGAATG GCTGCGTAAGAAGCTGCAGGATGTGCACAATTTTTAG

INFORMATION FOR SEQ ID NO 9:
(i) SEQUENCE CHARACTERISTICS:
(A) LENGTH: 104 bases (B) TYPE: Nucleic acid (oligonucleotide for synthesis for PTH(1-34))

(C) STRANDEDNESS: single (D) TOPOLOGY: linear

Seq id no 9:
CTAAAAATTGTGCACATCCTGCAGCTTCTTACGCAGCCATTCTACTCTCTCCATCGAG

TTCAGATGTTTTCCCAGGTTATGCATAAGCTGTATTTCCGACACCG

INFORMATION FOR SEQ ID NO 10:
(i) SEQUENCE CHARACTERISTICS:
(A) LENGTH: 42 bases (B) TYPE: Nucleic acid (Synthetic oligonucleotide)

(C) STRANDEDNESS: single (D) TOPOLOGY: linear

Seq id no 10:
GCGGATCCGATGATGATGATAAATCGGTGTCGGAAATACAGC

INFORMATION FOR SEQ ID NO 11:
(i) SEQUENCE CHARACTERISTICS:
(A) LENGTH: 34 bases (B) TYPE: Nucleic acid (Synthetic oligonucleotide)

(C) STRANDEDNESS: single (D) TOPOLOGY: linear

Seq id no 11:
TTATTGCTCAGCTCAAAAATTGTGCACATCTTGG

INFORMATION FOR SEQ ID NO 12 and 13
(i) SEQUENCE CHARACTERISTICS:
(A) LENGTH: 795 bases (B) TYPE: Nucleic acid (C) STRANDEDNESS: single (D) TOPOLOGY: linear (ii) FEATURE
(A) NAME/KEY: CDS (GCSF-PROINSULIN fusion protein)

(B) LOCATION: 1-792

(iii) FEATURE
(A) NAME/KEY: GCSF Fusion partner (B) LOCATION: 1-525

(iv) FEATURE
(A) NAME/KEY: Cyanogen bromide cleavage (Methionine)

(B) LOCATION: 532-534

(v) FEATURE
(A) NAME/KEY: PROINSULIN (1-34)

(B) LOCATION: 535-792

```
                                                      SEQ ID NO 12 and 13
  1  ATG ACT CCA TTA GGT CCA GCA AGC TCC CTG CCC CAG AGC TTC CTG       45
  1   M   T   P   L   G   P   A   S   S   L   P   Q   S   F   L       15

46  CTC AAG TGC TTA GAG CAA GTG AGG AAG ATC CAG GGC GAT GGC GCA       90
 16   L   K   C   L   E   Q   V   R   K   I   Q   G   D   G   A       30

91  GCG CTC CAG GAG AAG CTG TGT GCC ACC TAC AAG CTG TGC CAC CCC      135
 31   A   L   Q   E   K   L   C   A   T   Y   K   L   C   H   P       45
```

-continued

```
136 GAG GAG CTG GTG CTG CTC GGA CAC TCT CTG GGC ATC CCC TGG GCT   180
 46  E   E   L   V   L   L   G   H   S   L   G   I   P   W   A    60

181 CCC CTG AGC AGC TGC CCC AGC CAG GCC CTG CAG CTG GCA GGC TGC   225
 61  P   L   S   S   C   P   S   Q   A   L   Q   L   A   G   C    75

226 TTG AGC CAA CTC CAT AGC GGC CTT TTC CTC TAC CAG GGG CTC CTG   270
 76  L   S   Q   L   H   S   G   L   F   L   Y   Q   G   L   L    90

271 CAG GCC CTG GAA GGG ATC TCC CCC GAG TTG GGT CCC ACC TTG GAC   315
 91  Q   A   L   E   G   I   S   P   E   L   G   P   T   L   D   105

316 ACA CTG CAG CTG GAC GTC GCC GAC TTT GCC ACC ACC ATC TGG CAG   360
106  T   L   Q   L   D   V   A   D   F   A   T   T   I   W   Q   120

361 CAG ATG GAA GAA CTG GGG ATG GCC CCT GCC CTG CAG CCC ACC CAG   405
121  Q   M   E   E   L   G   M   A   P   A   L   Q   P   T   Q   135

406 GGT GCC ATG CCG GCC TTC GCC TCT GCT TTC CAG CGC CGG GCA GGA   450
136  G   A   M   P   A   F   A   S   A   F   Q   R   R   A   G   150

451 GGG GTC CTA GTT GCC TCC CAT CTG CAG AGC TTC CTG GAG GTG TCG   495
151  G   V   L   V   A   S   H   L   Q   S   F   L   E   V   S   165

496 TAC CGC GTT CTA CGC CAC CTT GCC CAG CCC GGA TCC     TTT GTG   540
166  Y   R   V   L   R   H   L   A   Q   P   G   S       F   V   180

541 AAC CAA CAC CTG TGC GGC TCA CAC CTG GTG GAA GCT CTC TAC CTA   585
181  N   Q   H   L   C   G   S   H   L   V   E   A   L   Y   L   195

586 GTG TGC GGG GAA CGA GGC TTC TTC TAC ACA CCC AAG ACC CGC CGG   630
196  V   C   G   E   R   G   F   F   Y   T   P   K   T   R   R   210

631 GAG GCA GAG GAC CTG CAG GTG GGG CAG GTG GAG CTG GGC GGG GGC   675
211  E   A   E   D   L   Q   V   G   Q   V   E   L   G   G   G   225

676 CCT GGT GCA GGC AGC CTG CAG CCC TTG GCC CTG GAG GGG TCC CTG   720
226  P   G   A   G   S   L   Q   P   L   A   L   E   G   S   L   240

721 CAG AAG CGT GGC ATT GTG GAA CAA TGC TGT ACC AGC ATC TGC TCC   765
241  Q   K   R   G   I   V   E   Q   C   C   T   S   I   C   S   255

766 CTC TAC CAG CTG GAG AAC TAC TGC AAC TAG                       795
256  L   Y   Q   L   E   N   Y   C   N   *
```

INFORMATION FOR SEQ ID NO 14:
(i) SEQUENCE CHARACTERISTICS:
(A) LENGTH: 32 bases (B) TYPE: Nucleic acid (Synthetic oligonucleotide)

(C) STRANDEDNESS: single (D) TOPOLOGY: linear

SEQ ID NO 14:
GCGGATCCATGTTTGTGAACCAGCATCTGTGC

INFORMATION FOR SEQ ID NO 15:
(i) SEQUENCE CHARACTERISTICS:
(A) LENGTH: 36 bases (B) TYPE: Nucleic acid (Synthetic oligonucleotide)

(C) STRANDEDNESS: single (D) TOPOLOGY: linear

SEQ ID NO 15:
TTATTGCTCAGCTTAGTTGCAATAGTTTTCCAGCTG

INFORMATION FOR SEQ ID NO 16 and 17:
(i) SEQUENCE CHARACTERISTICS:
(A) LENGTH: 579 bases (B) TYPE: Nucleic acid (C) STRANDEDNESS: single (D) TOPOLOGY: linear (ii) FEATURE
(A) NAME/KEY: CDS (GCSF-ANGIOTENSIN fusion protein)

(B) LOCATION: 1-576

(iii) FEATURE
(A) NAME/KEY: GCSF Fusion partner (B) LOCATION: 1-525

(iv) FEATURE
(A) NAME/KEY: Enterokinase Cleavage site (B) LOCATION: 532-546

(v) FEATURE
(A) NAME/KEY: Angiotensin (1-10)

(B) LOCATION: 547-576

```
                                                        SEQ ID NO 16 and 17
  1  ATG ACT CCA TTA GGT CCA GCA AGC TCC CTG CCC CAG AGC TTC CTG      45
  1   M   T   P   L   G   P   A   S   S   L   P   Q   S   F   L      15

46  CTC AAG TGC TTA GAG CAA GTG AGG AAG ATC CAG GGC GAT GGC GCA      90
 16   L   K   C   L   E   Q   V   R   K   I   Q   G   D   G   A      30

91  GCG CTC CAG GAG AAG CTG TGT GCC ACC TAC AAG CTG TGC CAC CCC     135
 31   A   L   Q   E   K   L   C   A   T   Y   K   L   C   H   P      45

136  GAG GAG CTG GTG CTG CTC GGA CAC TCT CTG GGC ATC CCC TGG GCT     180
 46   E   E   L   V   L   L   G   H   S   L   G   I   P   W   A      60

181  CCC CTG AGC AGC TGC CCC AGC CAG GCC CTG CAG CTG GCA GGC TGC     225
 61   P   L   S   S   C   P   S   Q   A   L   Q   L   A   G   C      75

226  TTG AGC CAA CTC CAT AGC GGC CTT TTC CTC TAC CAG GGG CTC CTG     270
 76   L   S   Q   L   H   S   G   L   F   L   Y   Q   G   L   L      90

271  CAG GCC CTG GAA GGG ATC TCC CCC GAG TTG GGT CCC ACC TTG GAC     315
 91   Q   A   L   E   G   I   S   P   E   L   G   P   T   L   D     105

316  ACA CTG CAG CTG GAC GTC GCC GAC TTT GCC ACC ACC ATC TGG CAG     360
106   T   L   Q   L   D   V   A   D   F   A   T   T   I   W   Q     120

361  CAG ATG GAA GAA CTG GGG ATG GCC CCT GCC CTG CAG CCC ACC CAG     405
121   Q   M   E   E   L   G   M   A   P   A   L   Q   P   T   Q     135

406  GGT GCC ATG CCG GCC TTC GCC TCT GCT TTC CAG CGC CGG GCA GGA     450
136   G   A   M   P   A   F   A   S   A   F   Q   R   R   A   G     150

451  GGG GTC CTA GTT GCC TCC CAT CTG CAG AGC TTC CTG GAG GTG TCG     495
151   G   V   L   V   A   S   H   L   Q   S   F   L   E   V   S     165

496  TAC CGC GTT CTA CGC CAC CTT GCC CAG CCC GGA TCC                 540
166   Y   R   V   L   R   H   L   A   Q   P   G   S                 180

541      GAT CGC GTG TAT ATT CAT CCG TTT CAT CTG TAG                 579
181       D   R   V   Y   I   H   P   F   H   L   *
```

INFORMATION FOR SEQ ID NO 18:
(i) SEQUENCE CHARACTERISTICS:
(A) LENGTH: 38 bases (B) TYPE: Nucleic acid (Synthetic oligonucleotide)

(C) STRANDEDNESS: single (D) TOPOLOGY: linear

SEQ ID NO 18:
CCCCTCTAGAAATAATTTTGTTTAACTTTAAGAAGGAG

INFORMATION FOR SEQ ID NO 19:
(i) SEQUENCE CHARACTERISTICS:
(E) LENGTH: 66 bases (F) TYPE: Nucleic acid (Synthetic oligonucleotide)

-continued (G) STRANDEDNESS: single (H) TOPOLOGY: linear

SEQ ID NO 19:
CGCCGAGTCGTCACAGATGAAACGGATGAATATACACGCGATCTTTATCATCA

TCATCGGATCCGC

---

SEQUENCE LISTING

<160> NUMBER OF SEQ ID NOS: 19

<210> SEQ ID NO 1
<211> LENGTH: 528
<212> TYPE: DNA
<213> ORGANISM: Homo sapiens

<400> SEQUENCE: 1

```
atgactccat taggtccagc aagctccctg ccccagagct tcctgctcaa gtgcttagag      60
caagtgagga agatccaggg cgatggcgca gcgctccagg agaagctgtg tgccacctac     120
aagctgtgcc accccgagga gctggtgctg ctcggacact ctctgggcat ccctgggct      180 cccctgagca gctgccccag ccaggccctg cagctggcag gctgcttgag ccaactccat     240
agcggccttt tcctctacca ggggctcctg caggccctgg aagggatctc ccccgagttg     300
ggtcccacct tggacacact gcagctggac gtcgccgact tgccaccac catctggcag     360 cagatggaag aactggggat ggcccctgcc ctgcagccca cccagggtgc catgccggcc     420
ttcgcctctg ctttccagcg ccgggcagga ggggtcctag ttgcctccca tctgcagagc     480
ttcctggagg tgtcgtaccg cgttctacgc accttgccc agccctga                   528
```

<210> SEQ ID NO 2
<211> LENGTH: 175
<212> TYPE: PRT
<213> ORGANISM: Homo sapiens

<400> SEQUENCE: 2

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

```
Phe Leu Glu Val Ser Tyr Arg Val Leu Arg His Leu Ala Gln Pro
            165                 170                 175
```

```
<210> SEQ ID NO 3
<211> LENGTH: 23
<212> TYPE: DNA
<213> ORGANISM: Artificial sequence
<220> FEATURE:
<223> OTHER INFORMATION: An artificially designed and synthetically
      generated Oligonucleotide

<400> SEQUENCE: 3
gcgcatatga ctccattagg tcc                                            23

<210> SEQ ID NO 4
<211> LENGTH: 32
<212> TYPE: DNA
<213> ORGANISM: Artificial sequence
<220> FEATURE:
<223> OTHER INFORMATION: An artificially designed and synthetically
      generated Oligonucleotide

<400> SEQUENCE: 4
gcggatcctc agggctgggc aaggtggcgt ag                                  32

<210> SEQ ID NO 5
<211> LENGTH: 29
<212> TYPE: DNA
<213> ORGANISM: Artificial sequence
<220> FEATURE:
<223> OTHER INFORMATION: An artificially designed and synthetically
      generated Oligonucleotide

<400> SEQUENCE: 5
gcggatccgg gctgggcaag gtggcgtag                                      29

<210> SEQ ID NO 6
<211> LENGTH: 651
<212> TYPE: PRT
<213> ORGANISM: Homo sapiens

<400> SEQUENCE: 6

Ala Thr Gly Ala Cys Thr Cys Cys Ala Thr Thr Ala Gly Gly Thr Cys
1               5                   10                  15

Cys Ala Gly Cys Ala Ala Gly Cys Thr Cys Cys Cys Thr Gly Cys Cys
            20                  25                  30

Cys Cys Ala Gly Ala Gly Cys Thr Thr Cys Cys Thr Gly Cys Thr Cys
        35                  40                  45

Ala Ala Gly Thr Gly Cys Thr Thr Ala Gly Ala Gly Cys Ala Ala Gly
    50                  55                  60

Thr Gly Ala Gly Gly Ala Ala Gly Ala Thr Cys Cys Ala Gly Gly Gly
65                  70                  75                  80

Cys Gly Ala Thr Gly Gly Cys Gly Cys Ala Gly Cys Gly Cys Thr Cys
                85                  90                  95

Cys Ala Gly Gly Ala Gly Ala Ala Gly Cys Thr Gly Thr Gly Thr Gly
            100                 105                 110

Cys Cys Ala Cys Cys Thr Ala Cys Ala Ala Gly Cys Thr Gly Thr Gly
        115                 120                 125

Cys Cys Ala Cys Cys Cys Gly Ala Gly Gly Ala Gly Cys Thr Gly
    130                 135                 140

Gly Thr Gly Cys Thr Gly Cys Thr Cys Gly Gly Ala Cys Ala Cys Thr
145                 150                 155                 160
```

-continued

```
Cys Thr Cys Thr Gly Gly Gly Cys Ala Thr Cys Cys Cys Cys Thr Gly
                165                 170                 175

Gly Gly Cys Thr Cys Cys Cys Cys Thr Gly Ala Gly Cys Ala Gly Cys
            180                 185                 190

Thr Gly Cys Cys Cys Cys Ala Gly Cys Cys Ala Gly Gly Cys Cys Cys
        195                 200                 205
Thr Gly Cys Ala Gly Cys Thr Gly Gly Cys Ala Gly Gly Cys Thr Gly
    210                 215                 220
Cys Thr Thr Gly Ala Gly Cys Cys Ala Ala Cys Thr Cys Cys Ala Thr
225                 230                 235                 240

Ala Gly Cys Gly Gly Cys Cys Thr Thr Thr Thr Cys Cys Thr Cys Thr
                245                 250                 255

Ala Cys Cys Ala Gly Gly Gly Gly Cys Thr Cys Cys Thr Gly Cys Ala
            260                 265                 270

Gly Gly Cys Cys Cys Thr Gly Gly Ala Ala Gly Gly Gly Ala Thr Cys
        275                 280                 285

Thr Cys Cys Cys Cys Cys Gly Ala Gly Thr Thr Gly Gly Gly Thr Cys
    290                 295                 300

Cys Cys Ala Cys Cys Thr Thr Gly Gly Ala Cys Ala Cys Ala Cys Thr
305                 310                 315                 320
Gly Cys Ala Gly Cys Thr Gly Gly Ala Cys Gly Thr Cys Gly Cys Cys
                325                 330                 335

Gly Ala Cys Thr Thr Thr Gly Cys Cys Ala Cys Cys Ala Cys Cys Ala
            340                 345                 350

Thr Cys Thr Gly Gly Cys Ala Gly Cys Ala Gly Ala Thr Gly Gly Ala
        355                 360                 365

Ala Gly Ala Ala Cys Thr Gly Gly Gly Gly Ala Thr Gly Gly Cys Cys
    370                 375                 380

Cys Cys Thr Gly Cys Cys Cys Thr Gly Cys Ala Gly Cys Cys Cys Ala
385                 390                 395                 400

Cys Cys Cys Ala Gly Gly Gly Thr Gly Cys Cys Ala Thr Gly Cys Cys
                405                 410                 415

Gly Gly Cys Cys Thr Thr Cys Gly Cys Cys Thr Cys Thr Gly Cys Thr
            420                 425                 430

Thr Thr Cys Cys Ala Gly Cys Gly Cys Cys Gly Gly Gly Cys Ala Gly
        435                 440                 445

Gly Ala Gly Gly Gly Gly Thr Cys Cys Thr Ala Gly Thr Thr Gly Cys
    450                 455                 460

Cys Thr Cys Cys Cys Ala Thr Cys Thr Gly Cys Ala Gly Ala Gly Cys
465                 470                 475                 480

Thr Thr Cys Cys Thr Gly Gly Ala Gly Gly Thr Gly Thr Cys Gly Thr
                485                 490                 495

Ala Cys Cys Gly Cys Gly Thr Thr Cys Thr Ala Cys Gly Cys Cys Ala
            500                 505                 510

Cys Cys Thr Thr Gly Cys Cys Cys Ala Gly Cys Cys Cys Gly Gly Ala
        515                 520                 525

Thr Cys Cys Gly Ala Thr Gly Ala Thr Gly Ala Thr Gly Ala Thr Ala
    530                 535                 540

Ala Ala Thr Cys Gly Gly Thr Gly Thr Cys Gly Gly Ala Ala Ala Thr
545                 550                 555                 560

Ala Cys Ala Gly Cys Thr Thr Ala Thr Gly Cys Ala Thr Ala Ala Cys
                565                 570                 575

Cys Thr Gly Gly Gly Ala Ala Ala Ala Cys Ala Thr Cys Thr Gly Ala
```

```
                580                 585                 590
Ala Cys Thr Cys Gly Ala Thr Gly Ala Gly Ala Gly Thr
            595                 600                 605

Ala Gly Ala Ala Thr Gly Gly Cys Thr Gly Cys Thr Ala Ala Gly
            610                 615                 620

Ala Ala Gly Cys Thr Gly Cys Ala Gly Gly Ala Thr Gly Thr Gly Cys
625                 630                 635                 640

Ala Cys Ala Ala Thr Thr Thr Thr Ala Gly
                645                 650

<210> SEQ ID NO 7
<211> LENGTH: 216
<212> TYPE: PRT
<213> ORGANISM: Homo sapiens

<400> SEQUENCE: 7

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Gly
                165                 170                 175

Ser Asp Asp Asp Asp Lys Ser Val Ser Glu Ile Gln Leu Met His Asn
            180                 185                 190

Leu Gly Lys His Leu Asn Ser Met Glu Arg Val Glu Trp Leu Arg Lys
        195                 200                 205

Lys Leu Gln Asp Val His Asn Phe
    210                 215

<210> SEQ ID NO 8
<211> LENGTH: 104
<212> TYPE: DNA
<213> ORGANISM: Artificial sequence
<220> FEATURE:
<223> OTHER INFORMATION: An artificially designed and synthetically
      generated Oligonucleotide

<400> SEQUENCE: 8
cggtgtcgga aatacagctt atgcataacc tgggaaaaca tctgaactcg atggagagag      60
tagaatggct gcgtaagaag ctgcaggatg tgcacaattt ttag                      104
```

```
<210> SEQ ID NO 9
<211> LENGTH: 104
<212> TYPE: DNA
<213> ORGANISM: Artificial sequence
<220> FEATURE:
<223> OTHER INFORMATION: An artificially designed and synthetically
      generated Oligonucleotide

<400> SEQUENCE: 9
ctaaaaattg tgcacatcct gcagcttctt acgcagccat tctactctct ccatcgagtt    60
cagatgtttt cccaggttat gcataagctg tatttccgac accg                    104

<210> SEQ ID NO 10
<211> LENGTH: 42
<212> TYPE: DNA
<213> ORGANISM: Artificial sequence
<220> FEATURE:
<223> OTHER INFORMATION: An artificially designed and synthetically
      generated Oligonucleotide

<400> SEQUENCE: 10
gcggatccga tgatgatgat aaatcggtgt cggaaataca gc                       42

<210> SEQ ID NO 11
<211> LENGTH: 34
<212> TYPE: DNA
<213> ORGANISM: Artificial sequence
<220> FEATURE:
<223> OTHER INFORMATION: An artificially designed and synthetically
      generated Oligonucleotide

<400> SEQUENCE: 11
ttattgctca gctcaaaaat tgtgcacatc ttgg                                34

<210> SEQ ID NO 12
<211> LENGTH: 795
<212> TYPE: DNA
<213> ORGANISM: Homo sapiens

<400> SEQUENCE: 12
atgactccat taggtccagc aagctccctg ccccagagct tcctgctcaa gtgcttagag    60
caagtgagga agatccaggg cgatggcgca gcgctccagg agaagctgtg tgccacctac   120
aagctgtgcc accccgagga gctggtgctg ctcggacact ctctgggcat cccctgggct   180
cccctgagca gctgccccag ccaggccctg cagctggcag gctgcttgag ccaactccat   240
agcggccttt tcctctacca ggggctcctg caggccctgg aagggatctc ccccgagttg   300
ggtcccacct tggacacact gcagctggac gtcgccgact tgccaccac catctggcag    360 cagatggaag aactggggat ggcccctgcc ctgcagccca cccagggtgc catgccggcc   420
ttcgcctctg ctttccagcg ccgggcagga ggggtcctag ttgcctccca tctgcagagc   480
ttcctggagg tgtcgtaccg cgttctacgc caccttgccc agcccggatc catgtttgtg   540
aaccaacacc tgtgcggctc acacctggtg gaagctctct acctagtgtg cggggaacga   600
ggcttcttct acacacccaa gacccgccgg gaggcagagg acctgcaggt ggggcaggtg   660
gagctgggcg ggggccctgg tgcaggcagc ctgcagccct ggccctgga ggggtccctg    720 cagaagcgtg gcattgtgga acaatgctgt accagcatct gctccctcta ccagctggag   780
aactactgca actag                                                    795

<210> SEQ ID NO 13
<211> LENGTH: 264
<212> TYPE: PRT
```

-continued

<213> ORGANISM: Homo sapiens

<400> SEQUENCE: 13

```
Met Thr Pro Leu Gly Pro Ala Ser Ser Leu Pro Gln Ser Phe Leu Leu
1               5                   10                  15
Lys Cys Leu Glu Gln Val Arg Lys Ile Gln Gly Asp Gly Ala Ala Leu
            20                  25                  30
Gln Glu Lys Leu Cys Ala Thr Tyr Lys Leu Cys His Pro Glu Glu Leu
        35                  40                  45
Val Leu Leu Gly His Ser Leu Gly Ile Pro Trp Ala Pro Leu Ser Ser
    50                  55                  60
Cys Pro Ser Gln Ala Leu Gln Leu Ala Gly Cys Leu Ser Gln Leu His
65                  70                  75                  80
Ser Gly Leu Phe Leu Tyr Gln Gly Leu Leu Gln Ala Leu Glu Gly Ile
                85                  90                  95
Ser Pro Glu Leu Gly Pro Thr Leu Asp Thr Leu Gln Leu Asp Val Ala
            100                 105                 110
Asp Phe Ala Thr Thr Ile Trp Gln Gln Met Glu Glu Leu Gly Met Ala
        115                 120                 125
Pro Ala Leu Gln Pro Thr Gln Gly Ala Met Pro Ala Phe Ala Ser Ala
    130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro Gly
                165                 170                 175
Ser Met Phe Val Asn Gln His Leu Cys Gly Ser His Leu Val Glu Ala
            180                 185                 190
Leu Tyr Leu Val Cys Gly Glu Arg Gly Phe Phe Tyr Thr Pro Lys Thr
        195                 200                 205
Arg Arg Glu Ala Glu Asp Leu Gln Val Gly Gln Val Glu Leu Gly Gly
    210                 215                 220
Gly Pro Gly Ala Gly Ser Leu Gln Pro Leu Ala Leu Glu Gly Ser Leu
225                 230                 235                 240
Gln Lys Arg Gly Ile Val Glu Gln Cys Cys Thr Ser Ile Cys Ser Leu
                245                 250                 255
Tyr Gln Leu Glu Asn Tyr Cys Asn
            260
```

<210> SEQ ID NO 14
<211> LENGTH: 32
<212> TYPE: DNA
<213> ORGANISM: Artificial sequence
<220> FEATURE:
<223> OTHER INFORMATION: An artificially designed and synthetically generated Oligonucleotide

<400> SEQUENCE: 14
gcggatccat gtttgtgaac cagcatctgt gc                                32

<210> SEQ ID NO 15
<211> LENGTH: 36
<212> TYPE: DNA
<213> ORGANISM: Artificial sequence
<220> FEATURE:
<223> OTHER INFORMATION: An artificially designed and synthetically generated Oligonucleotide

<400> SEQUENCE: 15
ttattgctca gcttagttgc aatagttttc cagctg                            36

<210> SEQ ID NO 16
<211> LENGTH: 579
<212> TYPE: DNA
<213> ORGANISM: Homo sapiens

<400> SEQUENCE: 16

| | | | | | |
|---|---|---|---|---|---|
| atgactccat | taggtccagc | aagctccctg | ccccagagct | tcctgctcaa | gtgcttagag | 60 |
| caagtgagga | agatccaggg | cgatggcgca | gcgctccagg | agaagctgtg | tgccacctac | 120 |
| aagctgtgcc | accccgagga | gctggtgctg | ctcggacact | ctctgggcat | ccctgggct | 180 |
| ccctgagca | gctgccccag | ccaggccctg | cagctggcag | gctgcttgag | ccaactccat | 240 |
| agcggccttt | tcctctacca | ggggctcctg | caggccctgg | aagggatctc | cccgagttg | 300 |
| ggtcccacct | tggacacact | gcagctggac | gtcgccgact | tgccaccac | catctggcag | 360 |
| cagatgaag | aactgggat | ggcccctgcc | ctgcagccca | cccagggtgc | catgccggcc | 420 |
| ttcgcctctg | ctttccagcg | ccgggcagga | ggggtcctag | ttgcctccca | tctgcagagc | 480 |
| ttcctggagg | tgtcgtaccg | cgttctacgc | caccttgccc | agcccggatc | cgatgatgat | 540 |
| gataaagatc | gcgtgtatat | tcatccgttt | catctgtag | | | 579 |

<210> SEQ ID NO 17
<211> LENGTH: 192
<212> TYPE: PRT
<213> ORGANISM: Homo sapiens

<400> SEQUENCE: 17

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Gly
                165                 170                 175

Ser Asp Asp Asp Asp Lys Asp Arg Val Tyr Ile His Pro Phe His Leu
            180                 185                 190

<210> SEQ ID NO 18
<211> LENGTH: 38
<212> TYPE: DNA
<213> ORGANISM: Artificial sequence
<220> FEATURE:
<223> OTHER INFORMATION: An artificially designed and synthetically

```
                                        -continued
        generated Oligonucleotide

<400> SEQUENCE: 18 ccccctctaga aataattttg tttaacttta agaaggag                             38

<210> SEQ ID NO 19
<211> LENGTH: 66
<212> TYPE: DNA
<213> ORGANISM: Artificial sequence
<220> FEATURE:
<223> OTHER INFORMATION: An artificially designed and synthetically
        generated Oligonucleotide

<400> SEQUENCE: 19
cgccgagtcg tcacagatga aacggatgaa tatacacgcg atctttatca tcatcatcgg     60
atccgc                                                                66
```

We claim:

1. A process for producing a peptide using Granulocyte Colony Stimulating Factor (GCSF) as a fusion partner wherein the GCSF is fused with a peptide of interest, comprising the steps of:
   a) constructing a GCSF expression vector;
   b) inserting the gene encoding the peptide of interest into the GCSF expression vector;
   c) transforming a host cell with the GCSF expression vector which causes the host cell to express the peptide of interest; and
   d) purifying the peptide of interest.

2. The process as claimed in claim 1, wherein GCSF forms a fusion product construct with the peptide.

3. The process as claimed in claim 2, wherein the fusion product construct is represented by the formula: Fusion partner-CS-Fusion peptide wherein the fusion peptide is the peptide of interest, CS is a suitable cleavage site, and the fusion partner is GCSF.

4. The process as claimed in claim 3, wherein the fusion peptide is a physiologically active peptide.

5. The process as claimed in claim 3, wherein the CS is either present within the fusion partner or the fusion peptide amino acid sequences or is a suitable linker.

6. The process as claimed in claim 3, wherein the fusion partner is linked at its C terminal end with a peptide at its N terminal end via a cleavage site.

7. The process as claimed in claim 4, wherein the physiologically active peptide is selected from those polypeptides having a length from about 10 amino acids to about 90 amino acids.

8. The process as claimed in claim 4, wherein the physiologically active peptides is selected from the group consisting of caltrin, calcitonin, insulin, angiotensin, tissue plasminogen activator, growth hormone, growth factors, growth hormone releasing factors, cytokines, erythropoietin, interferons, interleukins, oxytocin, vasopressin, ACTH, collagen binding protein, parathyroid hormone, glucagon like peptide, glucagon, proinsulin, tumor necrosis factor, substance P, brain naturetic peptide, individual heavy and light antibody chains, peptide antibiotics, fuzeon, octreotide, and somatostatin.

9. The process as claimed in claim 3, wherein the fusion product construct is cloned in a suitable expression vector.

10. The process as claimed in claim 9, wherein the fusion product construct is encoded by an expression vector that is able to express the fusion product in *E. coli*.

11. The process as claimed in claim 4, wherein the physiologically active peptide is selected from parathyroid hormone (PTH) (1-34), angiotensin and proinsulin.

12. The process as claimed in claim 11, wherein the physiologically active peptide is PTH (1-34) of SEQ ID NO:6.

13. The process as claimed in claim 11, wherein the physiologically active peptide PTH (1-34) is expressed by expression vector pET27B-GCSF-PTH deposited under MTCC Accession Number 5425.

14. The process as claimed in claim 11, wherein the physiologically active peptide is proinsulin of SEQ ID NO:13.

15. The process as claimed in claim 11, wherein the physiologically active peptide proinsulin is expressed by expression vector pET27B-GCSF-Proinsulin deposited under MTCC Accession Number 5424.

16. The process as claimed in claim 11, wherein the physiologically active peptide is angiotensin of SEQ ID NO:17.

17. The process as claimed in claim 11, wherein the physiologically active peptide angiotensin is expressed by expression vector pET27B-GCS F-Angiotensin.

18. The process as claimed in claim 3, wherein the cleavage site is an enzymatic or a chemical cleavage site.

19. The process as claimed in claim 18, wherein the cleavage site is a chemical cleavage site.

20. The process as claimed in claim 18, wherein the cleavage site is an enzymatic cleavage site.

21. The process as claimed in claim 19, wherein the cleavage site is cleavable by a chemical selected from cyanogen bromide, 2-(2-nitrophenylsulphenyl)-methyl-3'-bromoindolenine, BNPS-skatole, N-bromosuccinamide, O-iodosobenzoic acid, HBr/DMSO, NTCB, Ssodium metal in liquid ammonia, hydroxylamine and dilute acids.

22. The process as claimed in claim 21, wherein the chemical is cyanogen bromide.

23. The process as claimed in claim 20, where the enzymatic cleavage site is cleavable by an enzyme selected from enterokinase, trypsin, chymotrypsin, elastase, pepsin, papain, subtilisin, thermolysin, V8 protease, endoproteinase Arg C (submaxillaris protease), clostripain, thrombin, collagenase, lysobacter enzymogenes (Lys C), Mysobacter Al-I Protease and Factor Xa.

24. The process as claimed in claim 23, where the enzyme is enterokinase.

25. The process as claimed in claim 1, wherein step c) further comprises the steps of: disrupting the said host cell[s] and collecting a fusion protein comprising GCSF and the peptide of interest as inclusion bodies; separating the fusion protein containing inclusion bodies from other host components; solubilizing the fusion protein with a suitable denaturing agent; and cleaving a cleavage site with a suitable enzyme or chemical to release the peptide of interest.

26. The process as claimed in claim 25, wherein the host cell for the expression of the fusion product is *E. coli*.

27. The process as claimed in claim 1, wherein the GCSF fusion partner is encoded by the nucleotide sequence set forth in SEQ ID NaI.

* * * * *